United States Patent [19]
Guerrero et al.

[11] Patent Number: 5,236,710
[45] Date of Patent: Aug. 17, 1993

[54] COSMETIC COMPOSITION CONTAINING EMULSIFYING COPOLYMER AND ANIONIC SULFOSUCCINATE

[75] Inventors: Angel A. Guerrero, Huntington, Conn.; Anthony Vargas, Mahwah, N.J.

[73] Assignee: Elizabeth Arden Company, New York, N.Y.

[21] Appl. No.: 978,058

[22] Filed: Nov. 18, 1992

Related U.S. Application Data

[63] Continuation of Ser. No. 867,937, Apr. 13, 1992, abandoned.

[51] Int. Cl.⁵ .................... A61K 9/107; A61K 31/78; A61K 7/48
[52] U.S. Cl. .................... 424/401; 424/78.18; 424/78.02; 252/174.15; 252/554; 252/351; 252/DIG. 4; 252/DIG. 5; 514/944; 514/937
[58] Field of Search ................ 424/401, 70; 514/938

[56] References Cited

U.S. PATENT DOCUMENTS

| | | | |
|---|---|---|---|
| 4,717,498 | 1/1988 | Maxon | 252/174.15 |
| 4,777,277 | 10/1988 | Colas et al. | 556/419 |
| 4,849,127 | 7/1989 | Maxon | 252/174.15 |
| 5,004,598 | 4/1991 | Lochhead et al. | 424/59 |
| 5,035,890 | 7/1991 | Braun | 424/401 |

OTHER PUBLICATIONS

Product Brochure #TDS-114 entitled "Introducing Pemulen Polymeric Emulsifiers", BF Goodrich Company, Ohio, USA (1990).
Product Brochure #TDS-117 entitled "Skin Care Products Formulated with Pemulen Polymeric Emulsifiers", BF Goodrich Company, Ohio, USA (1990).
Product Brochure #TDS ∝ 118 entitled "Fragrance Products Formulated with Pemulen Polymeric Emulsifiers", BF Goodrich Company, Ohio, USA (1990).
Product Brochure for Mackanate DC-30, McIntyre Group, Ltd. Illinois, USA (1990).

*Primary Examiner*—Thurman K. Page
*Assistant Examiner*—Raj Bawa
*Attorney, Agent, or Firm*—Milton L. Honig

[57] ABSTRACT

A cosmetic composition is provided that includes an emulsifying copolymer formed from a major portion of a monoolefinically unsaturated carboxylic monomer and a minor portion of a long-chain acrylate or methacrylate ester monomer, a co-surfactant which is an anionic sulfosuccinate and a pharmaceutically acceptable vehicle. The preferred composition is in the form of a clear gel.

5 Claims, No Drawings

COSMETIC COMPOSITION CONTAINING EMULSIFYING COPOLYMER AND ANIONIC SULFOSUCCINATE

This is a continuation application of Ser. No. 07/8967,937 filed Apr. 13, 1992, now abandoned.

BACKGROUND OF THE INVENTION

Field of the Invention

The invention concerns a cosmetic composition for application to the human skin.

The Related Art

Considerable foreign material normally reaches and attaches to the skin. This foreign material may include both exogenous and autochthonous soils. The exogenous soils include those which reach the skin unintentionally, or that which is intentionally applied, such as ointments or cosmetics. Autochthonous soils are the products of excretion of the sebaceous, eccrine and apocrine glands. Cells and flakes of the cornified epithelium are also being shed continuously. Both society and health demand that these soils be removed from time to time. For abnormal skin there must also be removal of pus, blood cells, serous exudates and crusts.

Bathing with a soap bar is the usual manner for removing foreign material from the skin. Soap is, however, harsh. Neither does soap provide the softening, lubricating, protective or even exfoliating properties that are necessary for full treatment of the skin. A body rub formulation applied after bathing may provide the aforementioned properties missing from a mere treatment with soap.

A most important component of any body rub is that of a cleansing agent, especially a surfactant that is mild. Illustrative is U.S. Pat. No. 4,717,498 and U.S. Pat. No. 4,849,127, both to Maxon, which describe the use of dimethicone copolyol sulfosuccinate compounds as mild, foam-enhancing surfactants. Somewhat similar organosilicone sulfosuccinates are reported in U.S. Pat. No. 4,777,277 (Colas et al).

Phase stability for oil-in-water emulsions is another traditional objective for cosmetics with respect to aesthetic appeal. U.S. Pat. No. 5,004,598 (Lochhead et al) describes the use of lightly crosslinked modified polymers containing a small amount of a long chain acrylate ester comonomer. The modified polymer functions as an emulsifier rendering emulsions stable for long periods of time but also, imparts quick-breaking properties when the compositions contact an electrolyte or skin.

It is an object of the present invention to provide a cosmetic composition of excellent mildness for conditioning skin.

Another object of the present invention is to provide a cosmetic composition for use as a body rub to exfoliate skin.

Still a further object of the present invention is to provide a body rub exfoliator that is in the form of a clear gel so as to be aesthetically-pleasing to a consumer.

These and other objects, features and advantages of the present invention will become more readily apparent through consideration of the following summary, detailed description and examples which follow.

SUMMARY OF THE INVENTION

A cosmetic composition is provided comprising:
(i) from about 0.01 to about 30% by weight of a emulsifier which is a copolymer having a major portion of a monoolefinically unsaturated carboxylic acid or anhydride monomer of 3 to 6 carbon atoms and a minor portion of a long chain acrylate or methacylate ester monomer;
(ii) from about 0.01 to about 30% by weight of a co-surfactant which is an anionic sulfosuccinate;
(iii) from about 1 to about 99.95% of a pharmaceutically acceptable vehicle.

DETAILED DESCRIPTION

Now it has been discovered that a clear cosmetic composition that not only cleanses but is extremely mild can be provided through a combination surfactant system based upon an emulsifying copolymer and an anionic sulfosuccinate. A pharmaceutically acceptable vehicle is utilized as a carrier for this surfactant system.

A critical component of the present invention is that of an emulsifying copolymer. The copolymer is formed from a carboxylic monomer in an amount from about 50 to 99% by weight and a long chain acrylate ester in an amount from about 1 to 50% by weight. Amounts of the carboxylic monomer and the acrylate ester are based on the combined weight of both components. It should be understood that more than one carboxylic monomer and more than one acrylate ester can be used in the monomer charge.

Copolymers of this invention can be prepared from a monomeric mixture which contains two essential monomeric ingredients, each in certain proportions, one being a monomeric olefinically-unsaturated carboxylic monomer of 3 to 6 carbon atoms and the other being an acrylic ester having a long chain aliphatic group. Optionally, there is included in the monomeric mixture a crosslinking monomer. Amount of the carboxylic monomer is generally in a major proportion whereas the acrylic ester is used in a minor proportion. In a preferred embodiment, amount of the carboxylic monomer is 80 to 99%, but especially 90 to 98% by weight, whereas amount of the co-monomer is from 20 down to 1%, especially 10 down to 2% by weight, based on the weight of the two monomers.

The copolymers of a carboxylic monomer and an acrylic ester having a long chain aliphatic group can have polymerized therein a minor proportion of a lower alkyl ester of acrylic acid, such as ethyl acrylate, in amount of 0–40% by weight preferably 5–30%, based on the total a monomer charge.

The carboxylic monomers useful in the production of the copolymers of this invention are the olefinically-unsaturated carboxylic acids containing at least one activated carbon-to-carbon olefinic double bond, and at least one carboxyl group, that is, an acid containing an olefinic double bond which readily functions in polymerization because of its presence in the monomer molecule either in the alpha-beta position with respect to a carboxyl group or as a part of a terminal methylene grouping. The anhydrides can also be used, especially maleic anhydride.

The preferred carboxylic monomers for use in the copolymer are the monoolefinic acrylic acids having the general structure:

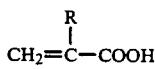

wherein R is a substitutent selected from the group consisting of hydrogen, halogen, hydroxyl, lactone, lactam, and the cyanogen (—C—N) groups, monovalent alkyl radicals, monovalent alkaryl radicals and monovalent cycloaliphatic radicals. Of this class, acrylic acid itself is most preferred because of its generally lower cost, ready availability, and ability to form superior polymers. Another particularly preferred carboxylic monomer is maleic anhydride.

The preferred acrylic ester monomers having long chain aliphatic groups are derivatives of acrylic acid reasserted by the formula:

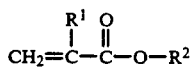

wherein $R^1$ is selected from hydrogen, methyl and ethyl groups and $R^2$ is selected from alkyl groups having from 8 to 30 carbon atoms and oxyacetylene and carbonyloxyalkylene groups, preferably alkyl groups of 10 to 22 carbon atoms. The oxyacetylene and carbonyloxyalkylene groups are particularly oxygehtylen and carbonyloxyethylene groups. Representative higher alkyl acrylic esters are decyl acrylate, lauryl acrylate, stearyl acrylate, behenyl acrylate and myristyl acrylate, and the corresponding methacrylates.

The modified polymers described herein, when tested in the form of 0.2% aqueous mucilages, have viscosity of 100 to 50,000 cps, preferably 250 to 40,000 cps and especially 500 to 35,000 cps. In the form of 1.0%, aqueous mucilages have viscosity of 1,000 to 100,000 cps, preferably 2,000 to 90,000 cps, and especially 2,500 to 85,000 cps. These viscosities are measured using the Brookfield RVT Model Viscometer at spindle speed of 20 rpm in the pH range of 7.2 to 7.6.

Commercially the emulsifying copolymers as described above are available from the B.F. Goodrich Company under the trademark Pemulen Tr-2$^{200}$. The CTFA name is acrylates/C10-C30 alkyl acrylate crosspolymer. Amounts of the copolymer used within the cosmetic compositions of this invention will range from about 0.1 to about 10%, preferably from about 0.5 to about 5% by weight.

Another important component of compositions according to the present invention is that of an anionic sulfosuccinate to serve as a co-surfactant. Amounts of the sulfosuccinate may range from about 0.01 to about 30%, preferably from about 0.5 to 20%, optimally between about 5 and 10% by weight. Both mono and diesters of sulfosuccinate may be utilized. Illustrative esters are the salts of cocamido MIPA sulfosuccinate, lauramido MEA sulfosuccinate, oleamido PEG-2 sulfosuccinate, oleamido MEA sulfosuccinate, ricinoleamido MEA sulfosuccinate, lauryl sulfosuccinate, laureth sulfosuccinate, oleth sulfosuccinate, undecylenamido MEA sulfosuccinate, palmitamido PEG-2 sulfosuccinate, palmitoleamido PEG-2 sulfosuccinate, deceth-6 sulfosuccinate, nonoxynol-10 sulfosuccinate, dioctyl sulfosuccinate, diamyl sulfosuccinate, and silicone copolyol sulfosuccinate. Salts of the aforementioned sulfosuccinates may be those of alkali metal, alkaline earth metal, ammonium, alkanolammonium and hydrogen. Particularly preferred is silicone copolyol sulfosuccinate available as Mackanate DC-30 and DC-30A from the McIntyre Chemical Company. Structures of silicone copolyol sulfosuccinates are set forth in U.S. Pat. No. 4,717,498 and U.S. Pat. No. 4,849,127, herein incorporated by reference.

The silicone copolyol sulfosuccinates are generally prepared by reacting the ethoxylated polyether side chains of dimethicone copolyol with maleic anhydride to form a monoester and then converting the monoester to sulfosuccinate by sulfonation of the double bond with a metallic sulfite. Metallic sulfite and amine salts may also be used either alone or in combination for sulfonation of the double bond. The resulting sulfosuccinate is a silicone-based surfactant which exhibits highly improved mildness and foam stabilizing properties.

Advantageously, compositions according to the present invention will contain an amphoteric surfactant which may be selected from alkyl and alkylamido betaines and from acylated α-amido acids. Preferred are $C_{10}$-$C_{18}$ alkyl $C_1$-$C_3$ dialkyl betaines and $C_{10}$-$C_{18}$ alkylamido alkyl betaines.

Amounts of the amphoteric surfactant may range from about 0.01 to about 30%, preferably from about 0.5 to about 10%, optimally between about 1 and about 5% by weight.

As the pharmaceutically acceptable vehicle, it is particularly advantageous to utilize a hydroxylic substance such as water. The vehicle may be present in amounts anywhere from about 1 to about 99.95%, preferably between about 40 and about 85%, optimally between about 50 and 70% by weight.

Vehicles other than water that can be used in compositions according to the invention can include liquids or solids such as emollients, solvents, humectants, thickeners and powders. Examples of each of these types of vehicles, which can be used singly or as mixtures of one or more vehicles, are as follows:

emollients, such as stearyl alcohol, oleyl alcohol, octadecan-2-ol, isocetyl alcohol, eicosanyl alcohol, behenyl alcohol, glyceryl monolaurate, glyceryl monoricinoleate, glyceryl monostearate, propane-1,2-diol, butane-1,3-diol, docosan-1,2-diol, mink oil, cetyl alcohol, isopropylisostearate, stearic acid, isobutyl palmitate, isocetyl stearate, isopropyl laurate, hexyl laurate, decyl oleate, cetyl palmitate, silicone oils such as dimethylpolysiloxane, di-n-butyl sebacate, isopropyl myristate, isopropyl palmitate, isopropyl stearate, butyl stearate, lanolin, cocoa butter, corn oil, cottonseed oil, tallow, lard, olive oil, palm kernel oil, rapeseed oil, safflower seed oil, soybean oil, sunflower seed oil, olive oil, sesame seed oil, coconut oil, arachis oil, castor oil, acetylated lanolin alcohols, petrolatum, mineral oil, butyl myristate, isostearic acid, stearic acid, palmitic acid, isopropyl linoleate, lauryl lactate, myristyl lactate, decyl oleate and myristate;

solvents such as ethyl alcohol, methylene chloride, isopropanol, acetone, castor oil, ethylene glycol monoethyl ether, diethylene glycol monobutyl ether, diethylene glycol monoethyl ether and dimethyl sulphoxide;

humectants such as glycerin, sorbitol, polyethylene glycol, triethylene glycol, soluble collagen, and gelatin;

powders such as chalk, talc, fullers earth, kaolin, starch, gums, colloidal silicon dioxide, sodium polyacrylate, tetra alkyl and/or trialkyl aryl ammonium smectites, chemically modified magnesium aluminium silicate, organically modified montmorillonite clay, hydrated aluminum silicate, fumed silica, carboxyvinyl polymer, sodium carboxymethyl cellulose and alkyl celluloses.

Although the cosmetic composition of this invention may be in liquid, powder, stick or other form, it is especially desirable to utilize a gel state. In fact, compositions of this invention are intended to be clear gels. Clarity is defined by its usual dictionary definition. Thus, a clear formulation, like glass, allows ready viewing of objects behind it. By contrast, a translucent formulation, although allowing light to pass through, causes the light to be so scattered as by a very small proportion of crystals or insolubles, that it will be impossible to clearly identify objects behind the translucent formulation. One test for clarity is to place a newspaper behind a sample 10 cm thick. If one is able to read print through the samples, then the composition is considered to be clear.

Another co-emulsifier also useful in the present invention is that of Polysorbate 20. Amounts of such material may range from about 0.1 to about 5% by weight.

When compositions of the present invention are used as exfoliant products, they may include such substances as hydrogenated jojoba oil, preferably in the form of wax beads. Of course, inorganic salts such as silicas, carbonates, phosphates, bromides and halides may also be utilized for such purpose. Normally present in compositions of this invention are preservatives, examples of which include methyl paraben, propyl paraben, imidazolidinyl urea, sodium dihydroxyacetate, benzyl alcohol, 2-phenoxyethanol, tetrasodium edetate and combinations thereof. Preservatives will usually be present in amounts ranging from about 0.5 to about 3% by weight of a composition.

Other adjunct minor components may also be incorporated into the cosmetic compositions. These ingredients may include coloring agents, opacifiers and perfumes. Amounts of these materials may range anywhere from about 0.001 up to 20% by weight.

The following examples will more fully illustrate the embodiments of this invention. All parts, percentages and proportions referred to herein and in the appended claims are by weight unless otherwise indicated.

EXAMPLE 1

Illustrative of the present invention is a sea salt body rub in the form of a gel having the formula listed below:

| Ingredients | Weight % |
| --- | --- |
| Deionized water | 70.3850 |
| Disodium dimethicone copolyol sulfosuccinate | 10.0000 |
| Jojoba beads (28/60 mesh) | 4.0000 |
| Cocamidopropyl betaine | 3.0000 |
| Butylene glycol | 3.0000 |
| Polysorbate 20 | 3.0000 |
| Triethanolamine, 99% | 1.9000 |
| Acrylates/C10-C30 Alkyl Acrylate Cross-Polymer | 1.4000 |
| Soothiplex 173 | 1.0000 |
| 2-Phenoxyethanol | 0.7000 |
| Benzyl alcohol NF | 0.5000 |
| Fragrance | 0.4500 |
| Methylparaben | 0.2000 |
| Seamollient | 0.1500 |
| Tetrasodium edetate | 0.1150 |
| Propylparaben | 0.1000 |

| Ingredients | Weight % |
| --- | --- |
| -continued | |
| Sea Salt | 0.1000 |

EXAMPLE 2

This Example investigates the use of other adrylate copolymers in the formulations of the present invention. Table I sets forth several compositions which were evaluated.

TABLE I

| | Formulations % | | | |
| --- | --- | --- | --- | --- |
| Ingredients | A | B | C | D |
| Carbopol 940 (2% sol.) | 65.00 | — | — | — |
| Carbopol 1342 (2% sol.) | — | 65.00 | — | — |
| Pemulen TR-1 (2% sol.) | — | — | 65.00 | — |
| Pemulen TR-2 (2% sol.) | — | — | — | 65.00 |
| Butylene glycol | 2.00 | 2.00 | 2.00 | 2.00 |
| Tween 20 | 1.00 | 1.00 | 1.00 | 1.00 |
| Mackanate DC-30 | 10.00 | 10.00 | 10.00 | 10.00 |
| Cocamidopropyl betaine | 3.00 | 3.00 | 3.00 | 3.00 |
| Deionized water | 17.00 | 17.00 | 17.00 | 17.00 |
| Triethanolamine, 99% | 2.00 | 2.00 | 2.00 | 2.00 |
| Total Weight % | 100.00 | 100.00 | 100.00 | 100.00 |

All four formulas provided a gel, however, only Formula D was clear; formula C was translucent and the other two gels (A and B) were cloudy. These results indicate that Pemulen TR-2 has special efficacy in providing clear compositions.

EXAMPLE 3

This Example evaluates the effectiveness of various sulfosuccinates. The base formula of Example 1 was herein utilized. Three expert panelists were chosen for the evaluation. Each of the panelists was asked to set the backs of their hands thoroughly prior to applying the test product. One gram of product was dispensed onto the back of the hands. A control was applied on one hand and a test product on the other hand. After application, the products were rubbed onto the skin so as to cover all of the est areas. Panelists were instructed to rub their hands for one minute. Excess product was removed with water and the test areas were patted dry. Process were evaluated on the basis of skin conditioning and afterfeel on the skin. Products were coded so that the panelists did not known which product the were applying. Table II sets forth the results; the (+) symbol indicates superior conditioning while the (−) symbol indicates inferior conditioning.

TABLE II

| Effect of Various Anionic Surfactants on Skin Conditioning | | | |
| --- | --- | --- | --- |
| | Panelist | | |
| Surfactant | No. 1 | No. 2 | No. 3 |
| Disodium laureth sulfosuccinate | — | — | — |
| Triethanolamine lauryl sulfate | — | — | — |
| Dimethicone copolyol sulfosuccinate | + | + | + |

From the results of Table II, it can be seen that only dimethicone copolyol sulfosuccinate in combination with Pemulen TR-2 was particularly effective in producing a high degree of skin conditioning.

The foregoing description and example illustrate selected embodiments of the present invention. In light thereof, various modifications will be suggested to one skilled in the art, all of which are within the spirit and purview of this invention.

What is claimed is:

1. A cosmetic composition comprising:
   (i) from about 0.01 to about 30% by weight of an emulsifier which is a copolymer having from about 50 to 99 % by weight of a monoolefinically unsaturated carboxylic acid or anhydride monomer of 3 to 6 carbon atoms and from about 1 to 50% by weight of a $C_{10}$–$C_{22}$ alkyl acrylate or methacylate ester monomer;
   (ii) from about 0.01 to about 30% by weight of a co-surfactant which is an anionic sulfosuccinate which is a silicone copolyol sulfosuccinate; and
   (iii) from about 1 to about 99.95% of a pharmaceutically acceptable vehicle.

2. A cosmetic composition according to claim 1 wherein the composition is in a clear gel form.

3. A cosmetic composition according to claim 2 wherein opaque beads are suspended in the clear gel.

4. A cosmetic composition in a clear gel from comprising:
   (i) from about 0.01 to about 30% by weight of an emulsifier which is a copolymer having from bout 50 to 99% by weight of a monoolefinically unsaturated carboxylic acid or anhydride monomer of 3 to 6 carbon atoms and from about 1 to 50% by weight of a $C_{10}$–$C_{22}$ alkyl acrylate or methacrylate ester monomer;
   (ii) from about 0.01 to about 30% by weight of a co-surfactant which is an anionic sulfosuccinate which is a silicone copolyol sulfosuccinate; and
   (iii) from about 1 to 99.95% of a pharmaceutically acceptable vehicle.

5. A cosmetic composition according to claim 4 comprising wax beads suspended in the clear gel.

* * * * *